US00PP10113P

United States Patent [19]

Twomey

[11] Patent Number: Plant 10,113

[45] Date of Patent: Nov. 11, 1997

[54] GRANDIFLORA ROSE PLANT VARIETY NAMED 'TWOCHERISH'

[75] Inventor: Jerry Twomey, Leucadia, Calif.

[73] Assignee: DeVor Nurseries, Inc., Watsonville, Calif.

[21] Appl. No.: 414,536

[22] Filed: Mar. 31, 1995

(Under 37 CFR 1.47)

[51] Int. Cl.[6] ..... A01H 5/00

[52] U.S. Cl. ..... Plt./20

[58] Field of Search ..... Plt./19, 20

*Primary Examiner*—Howard J. Locker

*Attorney, Agent, or Firm*—Christie, Parker & Hale, LLP

[57] ABSTRACT

A grandiflora rose variety producing coral red flowers.

1 Drawing Sheet

BACKGROUND OF THE INVENTION

The present invention relates to a new and distinct shrub rose variety which was originated by my crossing as seed parent an unnamed and undistributed seedling and as pollen parent the variety known as 'Silver Jubilee'. The new variety differs from 'Silver Jubilee' in growth habit and flower color. The flower of 'Silver Jubilee' are a pink blend with apricot and cream whereas the flower color of the new variety is coral red.

Among the novel characteristics possessed by this new variety which distinguish it from its parents and all other varieties of which I am aware are its attractive coral flowers borne on a bushy, vigorous plant. The varietal denomination of the new variety is 'Twocherish'.

Asexual reproduction by budding of the new variety as performed in Watsonville, Calif., shows that the foregoing and other distinguishing characteristics come true to form and are established and transmitted through succeeding propagations. Other known forms of asexual reproduction may be also employed.

BRIEF DESCRIPTION OF ILLUSTRATION

The accompanying illustration shows typical specimens of the vegetative growth and flowers of the new variety in different stages of development and depicted in color as nearly true as it is reasonably possible to make the same in a color illustration of this character.

DESCRIPTION OF THE NEW VARIETY

Parentage: Seedling.

*Seed parent.*—Unnamed, undistributed, and unpatented seedling.

*Pollen parent.*—"Silver Jubilee".

Class: Grandiflora.

The following is a detailed description of the new variety, from specimens grown outdoors in Watsonville, Calif., in the month of September. The color terminology used is in accordance with The Royal Horticultural Society Colour Chart (R.H.S.C.C.), and refers to plate numbers in the aforementioned color chart. Phenotypic expression may vary depending on light, environmental and cultural conditions.

FLOWER

Blooming habit: Recurrent.

A. Bud:

(1) *Size.*—Small.

(2) *Form.*—Pointed.

(3) *Color.*—When sepals first divide, bud color is near 50B.

(4) *Sepals.*—Longer than bud, spread when bloom opens; some sepals are foliaceous. Color: Upperside of sepals are near 146B with edges of near 178C. The underside of sepals are near 178C.

(5) *Peduncle.*—Length: About 4.5 cm to about 7 cm. Aspect: Small prickles. Strength: Erect, medium. Color: Near 146B with shading of near 178C.

(6) *Bracts.*—None observed.

B. Bloom:

(1) *Size.*—Average size when fully expanded—about 8 cm to about 9 cm.

(2) *Borne.*—Singly.

(3) *Form.*—Imbricated, informal, bloom flattens and petals reflex under slightly at maturity.

(4) *Petalage.* —Number of petals under normal conditions—about 29 to 35.

(5) *Color* (⅓–½ open).—After petals have unfurled and flower begins to open coloration appears near 46A where petals bunch. Upon opening to ½ to full open stage flower becomes more coral red in general coloration approaching from 53C to 53D. Some apices of outer petals exhibit darker red coloring. Petal undersurface is lighter in tonality, near 52C and 52D above the point of petal attachment. Base of petals: Near 2A. General tonality from a distance: Coral.

(6) *Color (fully open).*—Outer petals—Top surface: near 52A which fades to near 52D towards the apex; Undersurface; near 57B fading to near 58D towards apex. Inner petals—Top surface: ¼ of top is near 52A fading to near 52B towards apex; Undersurface: near 57C fading to near 58C towards apex Base of petals: Near 7A. General tonality from a distance: Coral.

(7) *Color change.*—As bloom ages, it lightens slightly. Petal top surface Lightens. Petal undersurface Acquires a more pink tone. General tonality at a distance Coral.

C. Petals:

(1) *Texture.*—Thick, smooth.

(2) *Appearance.*—Inside velvety and outside somewhat velvety.

(3 ) *Form.*—Wedge-shaped with curled apex.

(4) *Arrangement.*—Imbricated.

(5) *Petaloids.*—Very few.

(6) *Fragrance.*—Slightly fruity.

(7) *Lasting quality.*—On plant about 18 to 20 days about 7 to 10 days as cut flower.

(8) *Persistence.*—Petals drop off cleanly.

REPRODUCTIVE ORGANS

Stamens:

(1 ) *Arrangement.*—Regularly arranged around styles.
(2) *Stamens.*—Near 165B.
(3) *Anthers.*—Color near 22A.
(4) *Filaments.*—Near 34A with near 17A at base.
(5) *Pollen.*—Color—near 22A.

B. Pistils:

(1) *Styles.*—Bunched, uneven.
(2) *Stigmas.*—Color near 153D.

C. Characteristics of hips: Elongate, ovate, about 2 to 2.5 cm wide by about 1.5 to about 2 cm long, near 171C, seeds do not protrude.

PLANT

A. Form: Upright.
B. Growth: Very vigorous; about 90 cm to about 94 cm in height at first season.
C. Foliage: Compound 3 to 7 leaflets.

(1) *Size.*—Medium, similar to pollen parent.
(2) *Quantity.*—Abundant.
(3) *Color.*—New foliage—upper side near 137A underside near 146B, substantial red staining near, 187A, on both the upper and lower leaf surfaces in young foliage; mature foliage—upper side near 147A, underside near 147B.
(4) *Shape.*—Ovate.
(5) *Texture.*—Upper side leathery, glossy; underside leathery, matte.
(6) *Edge.*—Serrate.
(7) *Serration.*—Denticulate.
(8) *Leaf stem.*—Color—medium green.
(9) *Stipules.*—Medium length and width, parallel, auricle faces outward, slightly glandular.
(10) *Rachis.*—Small prickles on underside
(11) *Petioles.*—Top near 146A, underside near 146C .
(12) *Auricle.*—Stands straight: out, doesn't curl, slightly glandular.
(13) *Resistance to disease.*—Very resistant to blackspot, mildew and rust.

D. Wood:

(1) *New wood.*—Color near 176B, bark smooth with small prickles.
(2) *Old wood.*—Color near 146A, bark smooth, with large prickles, discolors in sun.

E. Flower stem: About 31 cm to about 41 cm from last cut.
F. Thorns:

(1) *Thorns.*—Quantity: On main stalk, average; laterals from stalk, some. Form: Thin, slightly curved downward. Length: Medium. Color: Near 161A. Position: Irregular.
(2) *Prickles.*—Many.

G. Winter hardiness: Winter hardy in Watsonville, Calif.

I claim:

1. A new and distinct grandiflora rose plant variety, substantially as shown and described.

* * * * *

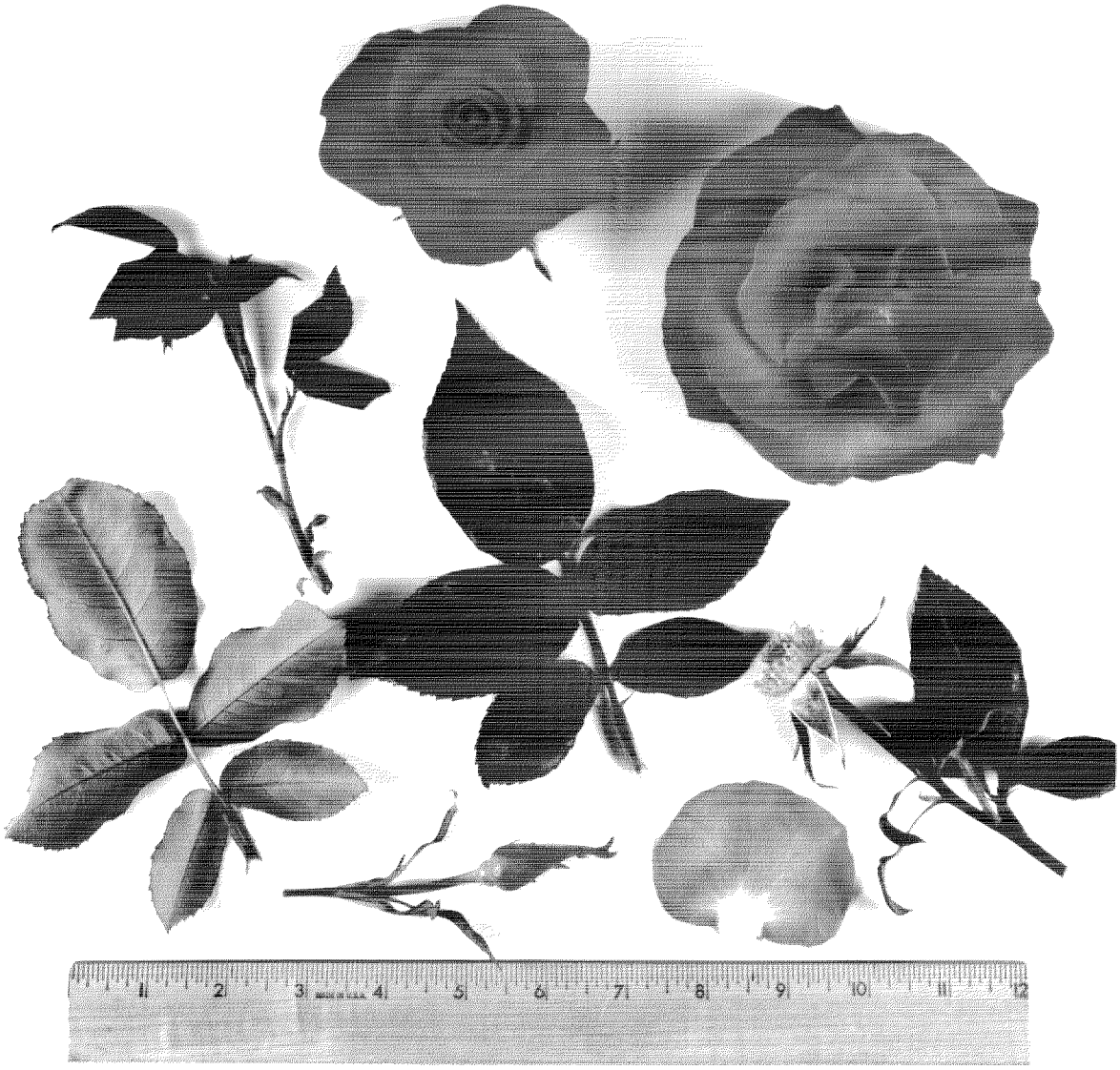
1
2
3
4
5
6
7
8
9
10
11
12